United States Patent [19]
Vanmaele

[11] Patent Number: 5,547,815
[45] Date of Patent: Aug. 20, 1996

[54] DYE DONOR ELEMENT FOR USE IN A THERMAL DYE TRANSFER METHOD

[75] Inventor: Luc Vanmaele, Lochristi, Belgium

[73] Assignee: Agfa-Gevaert, N.V., Mortsel, Belgium

[21] Appl. No.: 574,774

[22] Filed: Dec. 19, 1995

Related U.S. Application Data

[62] Division of Ser. No. 450,633, May 25, 1995.

[30] Foreign Application Priority Data

Jul. 4, 1994 [EP] European Pat. Off. ............... 94201905

[51] Int. Cl.⁶ .................................. G03C 1/73; G03C 8/10
[52] U.S. Cl. ........................ 430/338; 430/201; 430/339; 430/964; 503/227; 8/636
[58] Field of Search ..................... 430/200, 201, 430/338, 339, 964; 8/636; 503/227

[56] References Cited

U.S. PATENT DOCUMENTS 5,026,679  1/1991  Evans et al. .................. 430/201
5,169,828  12/1992  Janssens et al. .................. 503/227

*Primary Examiner*—Richard L. Schilling
*Attorney, Agent, or Firm*—Brumbaugh, Graves, Donohue & Raymond

[57] ABSTRACT

The present invention provides a dye donor element comprising a dye according to the following general formula:

wherein the symbols have a meaning as defined in the claims and the description. The present invention further provides a thermal dye transfer process using such dye donor elements. Furthermore, novel thermochromic compounds are provided.

5 Claims, No Drawings

DYE DONOR ELEMENT FOR USE IN A THERMAL DYE TRANSFER METHOD

This application is a division of application Ser. No. 08/450,633, filed on May 25, 1995, now pending.

DESCRIPTION

1. Field of the Invention

The present invention relates to dye-donor elements for use according to thermal dye sublimation transfer and to novel dyes for use in said dye-donor elements.

2. Background of the Invention

Thermal dye sublimation transfer or thermal dye diffusion transfer is a recording method in which a dye-donor element provided with a dye layer containing sublimable dyes having heat transferability is brought into contact with a receiver sheet or receiver element and selectively, in accordance with a pattern information signal, is heated by means of a thermal printing head provided with a plurality of juxtaposed heat-generating resistors. whereby dye is transferred from the selectively heated regions of the dye-donor element to the receiver sheet and forms a pattern thereon, the shape and density of which are in accordance with the pattern and intensity of heat applied to the dye-donor element.

A dye-donor element for use according to thermal dye sublimation transfer usually comprises a very thin support e.g. a polyester support, one side of which is covered with a dye layer comprising the printing dyes. Usually, an adhesive or subbing layer is provided between the support and the dye layer. Normally, the opposite side is covered with a slipping layer that provides a lubricated surface against which the thermal printing head can pass without suffering abrasion. An adhesive layer may be provided between the support and the slipping layer.

The dye layer can be a monochromic dye layer or it may comprise sequential repeating areas of differently coloured dyes e.g. dyes having a cyan, magenta, yellow, and optionally black hue. When a dye-donor element containing three or more primary colour dyes is used, a multicolour image can be obtained by sequentially performing the dye transfer process steps for each colour.

A primary coloured dye layer e.g. a magenta or cyan or yellow dye layer may comprise only one primary coloured dye (a magenta, cyan or yellow dye respectively) or may comprise a mixture of two or more primary colour dyes of the same hue (two magenta, two cyan or two yellow dyes respectively).

Any dye can be used in such a dye layer provided it is easily transferably to the dye-image-receiving layer of the receiver sheet or element by the action of heat.

Typical and specific examples of dyes for use in thermal dye sublimation transfer have been described in e.g. EP 209,990, EP 209,991, EP 216,483, EP 218,397, EP 227,095, EP 227,096, EP 229,374, EP 235,939, EP 247,737, EP 257,577, EP 257,580, EP 258,856, EP 279,330, EP 279,467, EP 285,665, U.S. Pat. No. 4,743,582, U.S. Pat. No. 4,753, 922, U.S. Pat. No. 4,753,923, U.S. Pat. No. 4,757,046, U.S. Pat. No. 4,769,360, U.S. Pat. No. 4,771,035, U.S. Pat. No. 5,026,677, JP 84/78,894, JP 84/78,895, JP 84/78,896, JP 84/227,490, JP 84/227,948, JP 85/27,594, JP 85/30,391, JP 85/229,787, JP 85/229,789, JP 85/229,790, JP 85/229,791, JP 85/229,792, JP 85/229,793, JP 85/229,795, JP 86/41,596, JP 86/268,493, JP 86/268,494, JP 86/268,495, and JP 86/284,489.

In spite of the many dyes that already exist, there is still a continuous search for novel dyes and especially for dyes that are suited for use in dye-donor elements for thermal dye sublimation transfer printing, preferably dyes with low melting points and a good solubility in ecologically acceptable solvents.

3. Summary of the Invention

It is therefore an object of the present invention to provide novel dye-donor elements for use according to thermal dye sublimation transfer printing.

It is another object of the present invention to provide novel dyes that can be used in said dye-donor elements.

Other objects will become apparent from the description hereinafter.

In accordance with the present invention a dye-donor element for use according to thermal dye sublimation transfer is provided, said dye-donor element comprising a support having Thereon a dye layer comprising a binder and a dye corresponding To the following general formula (I):

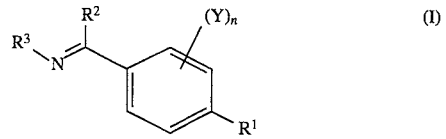

wherein:

$R^1$ represents $NR^4R^5$, $OR^6$ or $SR^6$, $R^2$ represents hydrogen, cyano $COR^7$, $CO_2R^7$, $CONR^8R^9$, $SO_2R^{10}$;

Y represents any substituent, e.g. SH, OH, $NH_2$, halogen, CN, $NO_2$, alkyl, alkoxy, thioalkoxy, carbonamido, sulfonamido, acylamino, sulfonylamino, carboxylic ester.

n represents 0, 1, 2, 3 or 4, the Y substituents being the same or different when n is greater Than 1 or the Y substituents can form an annelated ring system.

$R^3$ is the residue of a heterocyclic amine $R^3$—$NH_2$, $R^4$, $R^5$, $R^6$, $R^7$, $R^8$ and $R^9$ each independently represent hydrogen an alkyl, an alkenyl, an alkynyl, an aryl, a heterocyclic ring or $R^4$ and $R^5$ together represent the necessary atoms to form a 5- or 6-membered ring or $R^4$ and/or $R^5$ together with one of the Y-substituents represent the necessary atoms to form a 5- or 6-membered, fused-on heterocyclic ring system or $R^8$ and $R^9$ together represent the necessary atoms to form a 5- or 6-membered ring or $R^7$ or $R^8$ or $R^9$ or $R^8$ and $R^9$ together with one of the Y-substituents represent the necessary atoms to form a 5- or 6-membered, fused-on heterocyclic ring system.

$R^{10}$ represents hydroxy, alkoxy, aryloxy, $NR^{11}R^{12}$, aryl or alkyl or $R^{10}$ together with one of the Y-substituents represent the necessary atoms To form a 5- or 6-membered, fused-on heterocyclic ring system.

$R^{11}$ and $R^{12}$ each independently represent hydrogen, an alkyl, an alkenyl, an alkynyl, an aryl, a heterocyclic ring or $R^{11}$ and $R^{12}$ together represent The necessary atoms to form a 5- or 6-membered ring.

According to the present invention there are provided novel dyes according to the above general formula (I).

According to the present invention there is further provided a method for making an image according to the thermal dye transfer process comprising the steps of:

placing the dye layer of a dye donor element as defined above in face-to-face relationship with a dye-image receiving layer of a receiver sheet:

image-wise heating a thus obtained assemblage and separating said receiver sheet from said dye donor element.

In accordance with the present invention novel thermochromic compounds are provided, said thermochromic compounds corresponding to the following general formula (II):

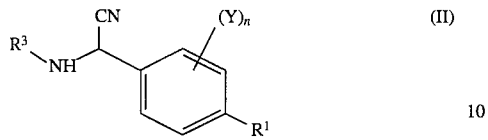

wherein:

$R^1$, $R^3$ and $(Y)_n$ have the same meaning as defined above. Preferentially $R^3$ represents thiazolyl, 4. Detailed Description of the Invention Preferred heteroaromatic amines $R^3$—$NH_2$ are those in which $R^3$ is selected from thiazoiyl, benzothiazolyl, isothiazolyl, benzoisothiazolyl, thienyl, pyridinyl, imidazolyl, benzimidazolyl, pyrazolyl, oxazolyl, thiadiazolyl, triazolyl, quinolyl, isoquinolyl, pyridoisothiazolyl, benzoxazolyl, isoxazolyl, benzoisoxazolyl, pyrrolyl, and isothiadiazolyl.

The residue, $R^3$, of the heteroaromatic amine, $R^3$—$NH_2$, may be substituted by non-ionic groups, preferably those which are free from acidic hydrogen atoms, unless these are positioned so that they form indramolecular hydrogen bonds.

Examples of suitable substituents are cyano, nitro, halogen, such as fluoro, chloro, bromo, alkyl, alkoxy, alkylthio, aryloxy, arylthio, formyl (—CHO), carboalkoxy, such as carbomethoxy, carboethoxy, tricyanovinyl (—C(CN)=C(CN)$_2$), —CH—N—$R^3$, —CH=CZ$^1$Z$^2$ where Z$^1$ and Z$^2$ independently represent an electron withdrawing group such as e.g. CN, carboalkoxy group, a carbonamido group, a carbonyl group etc., —SCN, an amino group such as e.g. dimethylamino, diethylamino, piperidino, pyrrolidino etc.

According to a preferred embodiment, the dyes of the present invention correspond to the following general formula (III):

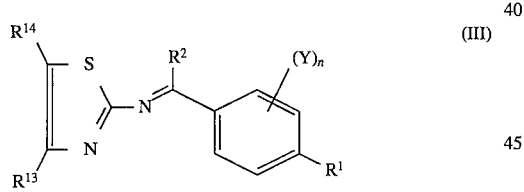

wherein:

$R^1$, $R^2$ and $(Y)_n$ have the same meaning as defined in the above general formula (I):

$R^{13}$ and $R^{14}$ each independently represent hydrogen, alkyl, aryl, alkenyl, alkynyl, alkoxy, aryloxy, thioalkyl, thioaryl, halogen, amino, $NO_2$, CN, acyloxy, acylamino, sulfonamido, sulfonylamino, a heterocyclic group, $POR^{15}R^{16}$, a sulfonyl group or $R^{17}$—C=A, $R^{15}$ and $R^{16}$ each independently represent alkyl, alkenyl, aryl. alkyloxy, aryloxy, alkylthio, arylthio, amino or a heterocyclic group or $R^{15}$ and $R^{16}$ together represent the necessary atoms to form a 5- or 6-membered ring, $R^{17}$ represents hydrogen, an alkyl, an aryl, an aryloxy group, an alkoxy group, e.g. methoxy or ethoxy, an alkylthio group, an amino group, an electron withdrawing group, e.g. CN, a halogen, a carboxylic ester, an amide e.g. carboxylamide, a sulphonate, a phosphonate, a carbonyl group, a nitro group or $R^{17}$ together with $R^{19}$, $R^{20}$ or $R^{18}$ represent the necessary atoms for completing a ring system, A represents O, N—$R^{18}$, $CR^{19}R^{20}$, $R^{18}$ represents H, CN, $NR^{21}R^{22}$, $OR^{21}$, $OCOR^{21}$, $OCO_2R^{21}$, $OCONR^{21}R^{22}$, $OSO_2R^{21}$, $OP(O)(OR^{21})(OR^{22})$ alkyl aryl a heterocyclic ring;

$R^{19}$ and $R^{20}$ independently represent a heterocyclic ring e.g. as defined for $R^3$ hereinbefore or an electron withdrawing group e.g. CN, a carboxylic ester, an amide e.g. carboxylamide, a sulphonate, a phosphonate, a carbonyl group, a nitro group or $R^{19}$ and $R^{20}$ together represent the necessary atoms for completing a ring system;

$R^{21}$ and $R^{22}$ independently represent hydrogen, alkyl, aryl, a heterocyclic ring e.g. as defined for $R^3$ hereinbefore, or $R^{21}$ and $R^{22}$ together represent the atoms necessary for completing a heterocyclic ring.

Representatives of novel dyes corresponding to general formula (III) are listed in table i hereinafter but are not limited thereto.

TABLE 1

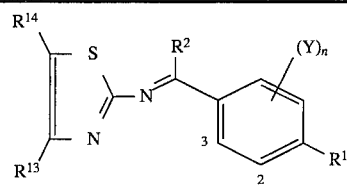

| Dye | $R^1$ | $R^2$ | $R^{13}$ | $R^{14}$ | n | Y |
|---|---|---|---|---|---|---|
| III.1 | $N(C_2H_5)_2$ | H | $OCH_3$ | CN | 0 | — |
| III.2 | $N(C_2H_5)_2$ | H | $OC_2H_5$ | CN | 0 | — |
| III.3 | $N(C_2H_5)_2$ | H | $OC_4H_9$ | CN | 0 | — |
| III.4 | $N(C_2H_5)_2$ | H | $N(C_2H_5)_2$ | CN | 0 | — |
| III.5 | $N(C_2H_5)_2$ | H | Fl | CN | 0 | — |
| III.6 | $N(C_2H_5)_2$ | H | F2 | CN | 0 | — |
| III.7 | $N(C_2H_5)_2$ | CN | $OC_4H_9$ | CN | 0 | — |
| III.8 | $N(C_2H_5)_2$ | CN | $OCH_3$ | CN | 0 | — |

TABLE 1-continued

| Dye | $R^1$ | $R^2$ | $R^{13}$ | $R^{14}$ | n | Y |
|---|---|---|---|---|---|---|
| III.9 | $N(C_2H_5)_2$ | CN | $OC_2H_5$ | CN | 0 | — |
| III.10 | $N(C_2H_5)_2$ | H | Cl | CHO | 0 | — |
| III.11 | $N(C_2H_5)_2$ | H | Cl | $CH=C(CN)_2$ | 0 | — |
| III.12 | $N(C_2H_5)_2$ | H | Cl | $C(CN)=C(CN)_2$ | 0 | — |
| III.13 | $N(C_2H_5)_2$ | H | $OCH_3$ | $CO_2CH_3$ | 0 | — |
| III.14 | $N(C_2H_5)_2$ | H | $OC_2H_5$ | $CO_2C_2H_5$ | 0 | — |
| III.15 | $N(C_2H_5)_2$ | CN | $OCH_3$ | $CO_2CH_3$ | 0 | — |
| III.16 | $N(C_2H_5)_2$ | CN | $OC_2H_5$ | $CO_2C_2H_5$ | 0 | — |
| III.17 | $N(C_2H_5)2$ | H | $OCH_3$ | CN | 1 | $3-CH_3$ |
| III.18 | $N(C_2H_5)_2$ | H | $OCH_3$ | CN | 1 | $3-OCH_3$ |
| III.19 | $N(C_2H_5)_2$ | H | $OCH_3$ | CN | 1 | $3-NHCOCH_3$ |
| III.20 | $N(C_2H_5)_2$ | CN | $OCH_3$ | CN | 1 | $3-CH_3$ |
| III.21 | $N-C_4H_9$ \| $CH(CH_3)C_2H_5$ | H | $OCH_3$ | CN | 0 | — |
| III.22 | $N-C_4H_9$ \| $CH(CH_3)C_2H_5$ | H | $OC_2H_5$ | CN | 0 | — |
| III.23 | $N-C_4H_9$ \| $CH(CH_3)C_2H_5$ | H | Fl | CN | 0 | — |
| III.24 | $N-C_4H_9$ \| $CH(CH_3)C_2H_5$ | CN | $OCH_3$ | CN | 0 | — |
| III.25 | $N-C_4H_9$ \| $CH(CH_3)C_2H_5$ | CN | $OC_2H_5$ | CN | 0 | — |
| III.26 | $N-C_4H_9$ \| $CH(CH_3)C_2H_5$ | CN | Fl | CN | 0 | — |
| III.27 | $N-C_4H_9$ \| $CH(CH_3)C_2H_5$ | $CO_2C_2H_5$ | $OCH_3$ | CN | 0 | — |
| III.28 | $N(C_4H_9)_2$ | H | $OCH_3$ | CN | 0 | — |
| III.29 | $N(C_4H_9)_2$ | H | $OC_2H_5$ | CN | 0 | — |
| III.30 | $N(C_4H_9)_2$ | H | $OC_4H_9$ | CN | 0 | — |
| III.31 | $N(C_4H_9)_2$ | CN | $OCH_3$ | CN | 0 | — |
| III.32 | $N(C_4H_9)_2$ | CN | $OC_2H_5$ | CN | 0 | — |
| III.33 | $N(C_4H_9)_2$ | CN | $OC_4H_9$ | CN | 0 | — |
| III.34 | $N(C_4H_9)_2$ | H | $OCH_3$ | CN | 1 | $3-CH_3$ |
| III.35 | $N(C_4H_9)_2$ | CN | $OCH_3$ | CN | 1 | $3-CH_3$ |
| III.36 | $N(C_4H_9)_2$ | CN | $OC_2H_5$ | CN | 1 | $3-CH_3$ |
| III.37 | $N(C_2H_5)_2$ | H | $OC_2H_5$ | $PO(OC_2H_5)_2$ | 0 | — |
| III.38 | $N(C_2H_5)_2$ | CN | $OC_2H_5$ | $PO(OC_2H_5)_2$ | 0 | — |
| III.39 | $N(C_2H_5)_2$ | $CO_2CH_3$ | $OCH_3$ | CN | 0 | — |
| III.40 | $N(C_2H_5)_2$ | $CO_2CH_3$ | $OC_2H_5$ | CN | 0 | — |
| III.41 | $N(C_2H_5)_2$ | $CO_2CH_3$ | Fl | CN | 0 | — |
| III.42 | $N(C_2H_5)_2$ | $CO_2C_2H_5$ | $OCH_3$ | CN | 0 | — |
| III.43 | $N(C_2H_5)_2$ | $CO_2C_2H_5$ | $OC_2H_5$ | CN | 0 | — |
| III.44 | $N(C_2H_5)_2$ | $CON(C_2H_5)_2$ | $OCH_3$ | CN | 0 | — |
| III.45 | $N(C_2H_5)_2$ | $CON(C_2H_5)_2$ | $OC_2H_5$ | CN | 0 | — |
| III.46 | $N(C_2H_5)_2$ | $CO_2C_2H_5$ | $OC_2H_5$ | $CO_2C_2H_5$ | 0 | — |
| III.47 | $N(C_2H_5)_2$ | H | Cl | $C=NOCH_3$ | 0 | — |
| III.48 | $N(C_2H_5)_2$ | H | Cl | CN | 0 | — |
| III.49 | $N(C_2H_5)_2$ | H | $C_6H_5$ | $CH_3$ | 0 | — |
| III.50 | $N(C_4H_9)_2$ | H | $OC_2H_5$ | CN | 1 | $3-CH_3$ |
| III.51 | $N(C_4H_9)_2$ | H | $OC_2H_5$ | $COOC_2H_5$ | 0 | — |
| III.52 | $N(C_4H_9)_2$ | H | $OC_2H_5$ | $COOC_2H_5$ | 1 | $3-CH_3$ |
| III.53 | $N-C_4H_9$ \| $CH(CH_3)C_2H_5$ | H | $OC_2H_5$ | $COOC_2H_5$ | 0 | — |

TABLE 1-continued

[Structure: R14-C(=C-R13)-S-C(=N-...)=N with =N-C(R2)=... attached to phenyl bearing (Y)n at position 3 and R1 at position 2/4]

| Dye | R¹ | R² | R¹³ | R¹⁴ | n | Y |
|---|---|---|---|---|---|---|
| III.54 | N(C₄H₉)₂ | CN | OC₂H₅ | COOC₂H₅ | 1 | 3-CH₃ |

III.55

III.56

III.57

III.58

III.59

TABLE 1-continued

[structure diagram with $R^{14}$, S, $R^2$, $(Y)_n$, $R^{13}$, N, $R^1$]

| Dye | $R^1$ | $R^2$ | $R^{13}$ | $R^{14}$ | n | Y |
|---|---|---|---|---|---|---|
| III.60 | | | | | | |
| III.61 | | | | | | |

[III.60: structure with NC, S, $CO_2C_2H_5$, $CH_3O$, N, morpholine ring]

[III.61: structure with CN, $CH_3O$, S, N, H, Cl, S, N, H, phenyl-N with $CH_3$, $CH_3$, $CH_3$ groups]

In the above table and following tables the residue $C_4H_9$ represents a n-butyl group and the fragments F1 and F2 have the following structure ("*" denotes the bonding position):

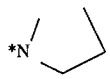
F1

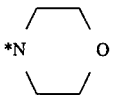
F2

According to another embodiment, the dyes of the present invention can be presented by the following general formula (IV):

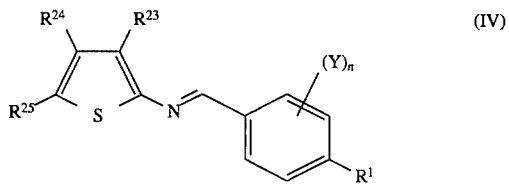
(IV)

wherein $R^1$, $R^2$ and $(Y)_n$ have the same meaning as defined in the above formula (I);

$R^{23}$ represents hydrogen, cyan or an electron withdrawing group such as a carboxylic ester, a carboxylic amide, a sulfonate, a phosphonate, a carbonyl group, a nitro group.

$R^{24}$ represents hydrogen, halogen, alkoxy, alkyl, aryl, amino, acylamino, CN, alkylthio, a carbocylic ester, a carboxylic amide, a sulfonate, a sulfonamide, a heterocyclic group e.g. such as defined for $R^3$ hereinbefore, an aryloxy, acyloxy, arylthio, an imino group, $R^{25}$ represents hydrogen, CN, alkyl, aryl, halogen, $NO_2$, a sulfonyl group, a sulfonate group, a sulfonamido group or $R^{17}$—C=A wherein $R^{17}$ and A have the same meaning as defined in formula (III), or $R^{24}$ and $R^{25}$ or $R^{24}$ and $R^{23}$ together represent the necessary atoms for completing a ring system.

Representatives of novel dyes corresponding to general formula (IV) are listed in tabel 2 hereinafter, but are not limited thereto.

TABLE 2

[Structure: thiophene ring with R25 at 5-position, R24 at 4-position, R23 at 3-position, and at 2-position N=C(R2)-phenyl group with (Y)n substituents and R1 at para position]

| Dye | $R^1$ | $R^2$ | $R^{23}$ | $R^{24}$ | $R^{25}$ | n | Y |
|---|---|---|---|---|---|---|---|
| IV.1 | $N(C_2H_5)_2$ | H | CN | $OC_2H_5$ | $CH_3$ | 0 | — |
| IV.2 | $N(C_2H_5)_2$ | H | CN | $NH_2$ | CN | 0 | — |
| IV.3 | $N(C_2H_5)_2$ | H | CN | $OC_2H_5$ | CHO | 0 | — |
| IV.4 | $N(C_2H_5)_2$ | H | CN | $OC_2H_5$ | $CH=C(CN)_2$ | 0 | — |
| IV.5 | $N(C_2H_5)_2$ | H | CN | $OC_2H_5$ | $C(CN)=C(CN)_2$ | 0 | — |
| IV.6 | $N(C_2H_5)_2$ | H | CN | $OC_2H_5$ | $C=NOCH_3$ | 0 | — |
| IV.7 | $N(C_2H_5)_2$ | H | CN | $OC_2H_5$ | CN | 0 | — |
| IV.8 | $N(C_2H_5)_2$ | H | CN | $OC_2H_5$ | $CH=C(CN)CO_2CH_3$ | 0 | — |
| IV.9 | $N(C_2H_5)_2$ | H | CN | $OCH_3$ | CHO | 0 | — |
| IV.10 | $N(C_2H_5)_2$ | H | CN | $OCH_3$ | $CH=C(CN)_2$ | 0 | — |
| IV.11 | $N(C_2H_5)_2$ | H | CN | $OCH_3$ | $C(CN)=C(CN)_2$ | 0 | — |
| IV.12 | $N(C_2H_5)_2$ | H | CN | $OCH_3$ | CN | 0 | — |
| IV.13 | $N(C_2H_5)_2$ | H | CN | $OCH_3$ | $C_6H_5$ | 0 | — |
| IV.14 | $N(C_4H_9)_2$ | H | CN | $OC_2H_5$ | $CH_3$ | 0 | — |
| IV.15 | $N(C_4H_9)_2$ | H | CN | $OC_2H_5$ | $CH_3$ | 1 | 3-$CH_3$ |
| IV.16 | $N(C_4H_9)_2$ | H | CN | $OCH_3$ | CHO | 0 | — |
| IV.17 | $N(C_4H_9)_2$ | H | CN | $OCH_3$ | $CH=C(CN)_2$ | 0 | — |
| IV.18 | $N(C_4H_9)_2$ | H | CN | $OCH_3$ | $C(CN)=C(CN)_2$ | 0 | — |
| IV.19 | $N(C_2H_5)_2$ | H | CN | $NH_2$ | CN | 0 | — |
| IV.20 | $N(C_4H_9)_2$ | H | CN | $OCH_3$ | CN | 0 | — |
| IV.21 | $N(C_4H_9)$-$CH(CH_3)C_2H_5$ | H | CN | $OCH_3$ | $CH_3$ | 0 | — |
| IV.22 | $N(C_4H_9)$-$CH(CH_3)C_2H_5$ | H | CN | $OCH_3$ | $C_6H_5$ | 0 | — |
| IV.23 | $N(C_4H_9)$-$CH(CH_3)C_2H_5$ | H | CN | $OCH_3$ | CHO | 0 | — |
| IV.24 | $N(C_4H_9)$-$CH(CH_3)C_2H_5$ | H | CN | $OCH_3$ | CN | 0 | — |
| IV.25 | $N(C_4H_9)$-$CH(CH_3)C_2H_5$ | H | CN | $OCH_3$ | $CH=C(CN)_2$ | 0 | — |
| IV.26 | $N(C_4H_9)$-$CH(CH_3)C_2H_5$ | H | CN | $OCH_3$ | $C(CN)=C(CN)_2$ | 0 | — |
| IV.27 | $N(C_4H_9)$-$CH(CH_3)C_2H_5$ | H | CN | $OC_2H_5$ | $CH_3$ | 0 | — |
| IV.28 | $N(C_4H_9)$-$CH(CH_3)C_2H_5$ | H | $CO_2CH_3$ | $OCH_3$ | $CH_3$ | 0 | — |
| IV.29 | $N(C_2H_5)_2$ | H | $CO_2CH_3$ | $OCH_3$ | $CH_3$ | 0 | — |
| IV.30 | $N(C_2H_5)_2$ | CN | CN | $OCH_3$ | $CH_3$ | 0 | — |
| IV.31 | $N(C_2H_5)_2$ | CN | CN | $OCH_3$ | CHO | 0 | — |
| IV.32 | $N(C_2H_5)_2$ | CN | CN | $OCH_3$ | $C(CN)=C(CN)_2$ | 0 | — |
| IV.33 | $N(C_2H_5)_2$ | CN | CN | $OCH_3$ | $C=NOCH_3$ | 0 | — |
| IV.34 | $N(C_2H_5)_2$ | H | CN | $OCH_3$ | $NO_2$ | 0 | — |
| IV.35 | $N(C_2H_5)_2$ | H | CN | $CH_3$ | $CO_2C_2H_5$ | 0 | — |

TABLE 2-continued

[Structure: thiophene with R24, R23, R25, R2, N=C to phenyl ring with (Y)n and R1]

| Dye | R1 | R2 | R23 | R24 | R25 | n | Y |
|---|---|---|---|---|---|---|---|
| IV.36 | | | | | | | |
| IV.37 | | | | | | | |
| IV.38 | | | | | | | |
| IV.39 | | | | | | | |

TABLE 2-continued

| Dye | R¹ | R² | R²³ | R²⁴ | R²⁵ | n | Y |
|---|---|---|---|---|---|---|---|
| IV.40 | | | CH₃O | CN | | | |

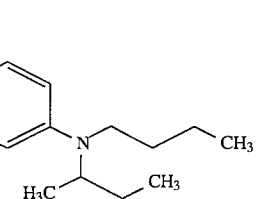

According to another embodiment, the dyes of the present invention can be represented by the following general formulas (V) and (VI):

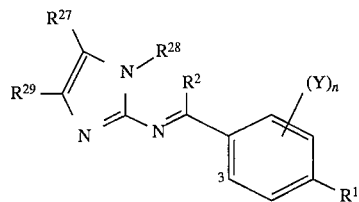  (V)

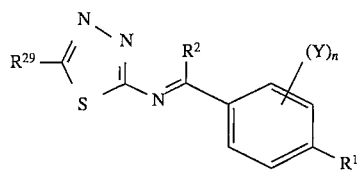  (VI)

In the above formulas (V) and (VI) $R^1$, $R^2$, Y and n have the same meaning as defined in the above formula (I):

$R^{26}$ and $R^{27}$ each independently represent hydrogen, alkyl, aryl, alkenyl, alkynyl, alkoxy, aryloxy, thioalkyl, thioaryl, halogen, $NO_2$, CN, acyloxy, acylamino, sulfonamido, sulfonylamino, a heterocyclic group, $POR^{15}R^{16}$, a sulfonyl group or $R^{17}$—C=A, $R^{15}$, $R^{16}$, $R^{17}$ and A have the same meaning as defined in formula (III):

$R^{28}$ represents hydrogen, alkyl, aryl, acyl or sulfonyl;

$R^{27}$ and $R^{28}$, or $R^{26}$ and $R^{27}$ together represent the necessary atoms for completing a ring system and $R^{29}$ represents any substituent.

Representatives of novel dyes corresponding to general formulas (V) and (VI) are listed in tabel 3 and 4 hereinafter.

TABLE 3

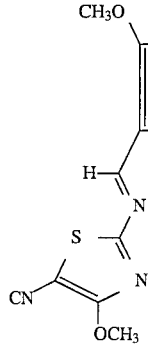

| Dye | R¹ | R² | R²⁸ | R²⁶ | R²⁷ | n | Y |
|---|---|---|---|---|---|---|---|
| V.1 | N(C₂H₅)₂ | H | CH₃ | Cl | CHO | 0 | — |
| V.2 | N(C₂H₅)₂ | CN | CH₃ | Cl | CHO | 0 | — |
| V.3 | N(C₂H₅)₂ | H | CH₃ | OCH₃ | CHO | 0 | — |
| V.4 | N(C₂H₅)₂ | H | CH₃ | OCH₃ | C=NOCH₃ | 0 | — |
| V.5 | N(C₂H₅)₂ | H | CH₃ | OCH₃ | CN | 0 | — |
| V.6 | N(C₂H₅)₂ | H | CH₃ | OCH₃ | CH=C(CN)₂ | 0 | — |
| V.7 | N(C₂H₅)₂ | H | CH₃ | OCH₃ | C(CN)=C(CN)₂ | 0 | — |
| V.8 | N(C₂H₅)₂ | H | CH₃ | Cl | CN | 0 | — |
| V.9 | N(C₂H₅)₂ | H | CH₃ | Cl | CH=C(CN)₂ | 0 | — |

TABLE 3-continued
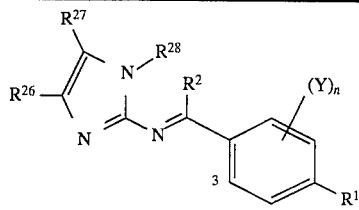
| Dye | R¹ | R² | R²⁸ | R²⁶ | R²⁷ | n | Y |
|---|---|---|---|---|---|---|---|
| V.10 | N(C₂H₅)₂ | H | CH₃ | Cl | C(CN)=C(CN)₂ | 0 | — |
| V.11 | N(C₂H₅)₂ | H | CH₃ | Cl | CHO | 1 | 3-CH₃ |
| V.12 | N(C₂H₅)₂ | H | CH₃ | Cl | CHO | 1 | 3-OCH₃ |
| V.13 | N(C₄H₉)₂ | H | CH₃ | Cl | CHO | 0 | — |
| V.14 | N(C₄H₉)₂ | H | CH₃ | Cl | CN | 0 | — |
| V.15 | N(C₄H₉)₂ | H | CH₃ | Cl | C=NOCH₃ | 0 | — |
| V.16 | N(C₄H₉)₂ | CO₂C₂H₅ | CH₃ | Cl | CHO | 0 | — |
| V.17 | N(C₄H₉)₂ | H | CH₃ | CN | CN | 0 | — |
V.18
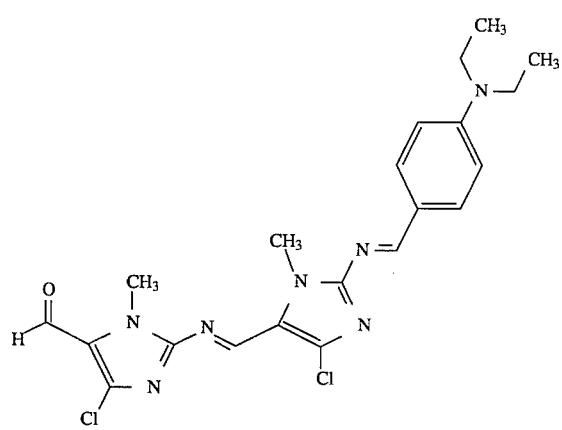
V.19
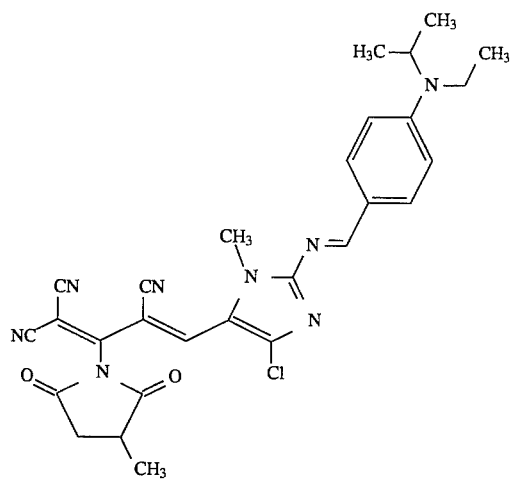

TABLE 3-continued
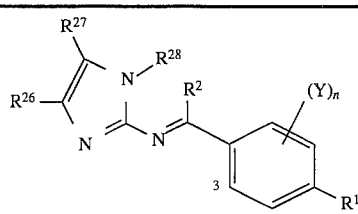
| Dye | R¹ | R² | R²⁸ | R²⁶ | R²⁷ | n | Y |
|---|---|---|---|---|---|---|---|
V.20
V.21
TABLE 4
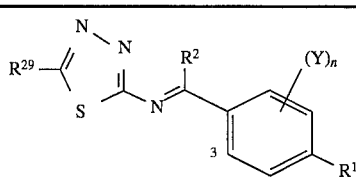
TABLE 4-continued
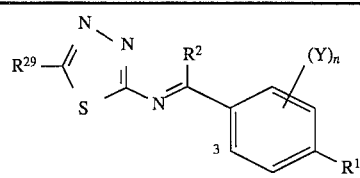
| Dye | R¹ | R² | R²⁹ | n | Y |
|---|---|---|---|---|---|
| VI.1 | N(C₂H₅)₂ | H | F 3 | 0 | — |
| VI.2 | N(C₂H₅)₂ | H | CH₃ | 0 | — |
| VI.3 | N(C₂H₅)₂ | H | OC₂H₅ | 0 | — |
| VI.4 | N(C₂H₅)₂ | H | H | 0 | — |
| VI.5 | OCH₃ | H | SH | 0 | — |
| VI.6 | N(C₄H₉)₂ | H | OC₂H₅ | 1 | 3-CH₃ |
| VI.7 | N(C₄H₉)₂ | H | CH₃ | 0 | — |
| VI.8 | N(C₄H₉)₂ | H | CH₃ | 1 | 3-CH₃ |
| VI.9 | N—C₄H₉ \| CH(CH₃)C₂H₅ | H | CH₃ | 0 | — |
| VI.10 | N—C₄H₉ \| CH(CH₃)C₂H₅ | H | OC₂H₅ | 0 | — |
| VI.11 | N—C₄H₉ \| CH(CH₃)C₂H₅ | CN | OC₂H₅ | 0 | — |
| VI.12 | N—C₄H₉ \| CH(CH₃)C₂H₅ | CO₂C₂H₅ | OC₂H₅ | 0 | — |
| VI.13 | N—C₄H₉ \| CH(CH₃)C₂H₅ | H | C(CH₃)₃ | 0 | — |

TABLE 4-continued
| Dye | R¹ | R² | R²⁹ | n | Y |
|---|---|---|---|---|---|
| VI.14 | N—C₄H₉ \| CH(CH₃)C₂H₅ | H | SC₂H₅ | 0 | — |
In the above table F3 corresponds to the following structure with "*" denoting the bonding position:
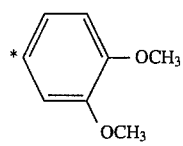
F3
Other representatives of dyes corresponding to general formula I are listed in tabel 5 hereinafter and are not limited thereto.

TABLE 5-continued

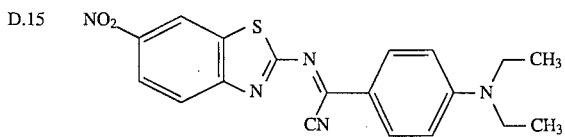

D.15

According to a further aspect of the present invention, the dyes according to formula (I) can be converted into a thermochromic compound of formula (II) by an addition with a cyanide ion. Representatives of thermochromic compounds of general formula (II) are listed in table 6. Upon heating these leuco compounds are transformed back into the original dyes of general formula (I), as shown below:

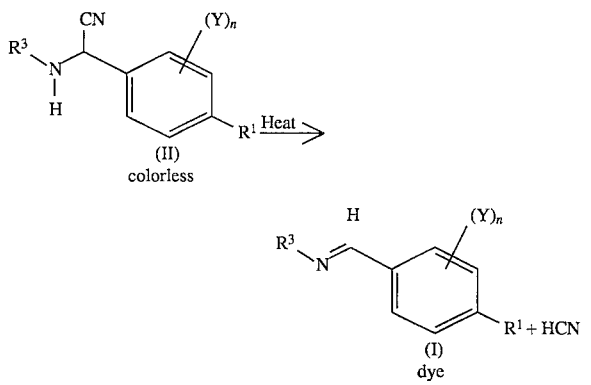

TABLE 6

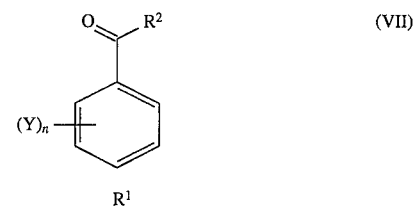

| Compound | $R^1$ | $R^{13}$ | $R^{14}$ | n | Y |
|---|---|---|---|---|---|
| II.1 | $N(C_2H_5)_2$ | $OCH_3$ | CN | 0 | — |
| II.2 | $N(C_2H_5)_2$ | $OC_2H_5$ | CN | 0 | — |
| II.3 | $N(C_2H_5)_2$ | $OC_4H_9$ | CN | 0 | — |
| II.4 | $N-C_4H_9$ $\mid$ $CH(CH_3)C_2H_5$ | $OCH_3$ | CN | 0 | — |
| II.5 | $N-C_4H_9$ $\mid$ $CH(CH_3)C_2H_5$ | $OC_2H_5$ | CN | 0 | — |
| II.6 | $N(C_4H_9)_2$ | $OCH_3$ | CN | 0 | — |
| II.7 | $N(C_4H_9)_2$ | $OC_2H_5$ | CN | 0 | — |
| II.8 | $N(C_4H_9)_2$ | $OCH_3$ | CN | 1 | $3\text{-}CH_3$ |
| II.9 | $N(C_4H_9)_2$ | $OC_2H_5$ | CN | 1 | $3\text{-}CH_3$ |
| II.10 | $N(C_4H_9)_2$ | $OC_2H_5$ | $CO_2C_2H_5$ | 0 | — |

The dyes according to the present invention have a cyan, magenta, or yellow hue or absorb in the UV or IR-region, and have a good solubility in ecologically acceptable organic solvents such as e.g. ethyl acetate and ethyl methyl ketone. Dyes according to the present invention absorbing in the IR-region, i.e. above 700 nm, are suitable as light-stabilisers for a dye image formed in accordance with the present invention.

The dyes of formula (I) can be prepared by well known chemical synthetic techniques, for example, by a condensation reaction between a heterocyclic amine $R^3$—$NH_2$ and a carbonyl compound of general formula (VII):

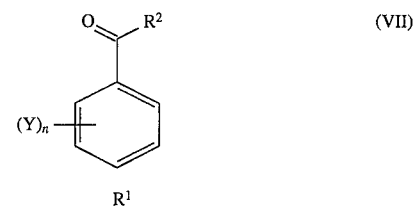

(VII)

wherein $R^1$, $R^2$ and $(Y)_n$ have the same meaning as defined in the above general formula (I).

Examples of heterocyclic amines $R^3$—$NH_2$ are mentioned above, e.g. thiazoles, imidazoles, oxazoles, thiophenes, pyrroles, thiadiazoles etc. The synthesis and modification of these amines is well known in chemical literature e.g. "The chemistry of heterocyclic compounds", a series of monographs, Wiley & Sons: Pyrroles, Part one and two, edited by R. Alan Jones (Wiley & Sons): Thiazole and its derivatives Part two, edited by J. V. Metzger (Wiley & Sons): Z.Chem. 27(7), pages 258–259 (1987): GB 1497537: Handbook of Heterocyclic Chemistry. Allan R. Katritzky, Pergamon Press (1985): EP 193885.

Carbonyl compounds of general formula (VII) are usually commercially available or can be prepared by well known synthetic methods. The synthesis of dyes according to formula (I) is described below in further detail in the examples.

The dyes corresponding to the general formulas (I) and (III) to (VI) defined above can be used in inkjer printing, resistive ribbon printing, in inks e.g. for laser applications, in textile, in lacquers, and in paints. They can also be used for transfer printing on fabrics and for constructing filter array elements. According to a preferred embodiment of the present invention the dyes are used in the dye layer of a dye-donor element for thermal dye sublimation transfer.

To improve the stability of the dyes to light, the use of a metal complex of the dye e.g. a Ni or Co complex is also effective.

The dye layer is formed preferably by adding the dyes, the polymeric binder medium, and other optional components to a suitable solvent or solvent mixture, dissolving or dispersing the ingredients to form a coating composition that is applied to a support, which may have been provided first with an adhesive or subbing layer, and dried.

The dye layer thus formed has a thickness of about 0.2 to 5.0 µm, preferably 0.4 to 2.0 µm, and the amount ratio of dye to binder ranges from 9:1 To 1:3 by weight, preferably from 2:1 to 1:2 by weight.

As polymeric binder the following can be used : cellulose derivatives, such as ethyl cellulose, hydroxyethyl cellulose, ethylhydroxy cellulose, ethylhydroxyethyl cellulose, hydroxypropyl cellulose, methyl cellulose, cellulese nitrate, cellulose acetate formate, cellulose acetate hydrogen phthalate, cellulose acetate, cellulose acetate propionate, cellulose acetate butyrate, cellulose acetate pentanoate, cellulose acetate benzoate, cellulose triacetate; vinyl-type resins and derivatives, such as polyvinyl alcohol, polyvinyl acetate, polyvinyl butyral, copolyvinyl burytel-vinyl acetel-vinyl alcohol, polyvinyl pyrrolidone, polyvinyl acetoacetal, polyacrylamide; polymers and copolymers derived from acrylates and acrylate derivatives, such as polyacrylic acid, polymethyl methacrylate and styrene-acrylate copolymers; polyester resins; polycarbonates; copolystyrene-acrylonitrile; polysulfones; polyphenylene oxide; organosilicones, such as polysiloxanes; epoxy resins and natural resins, such as gum arabic. Preferably, the binder for the dye layer of the present invention comprises cellulose acetate butyrate of copolystyrene-acrylonitrile.

The dyes in accordance with the present invention may be used in admixture with other known dyes for thermal sublimation printing. In particular they can be used in combination with tricyano- and dicyanovinyl dyes as disclosed in EP 92203566, EP 92203208 and with malononitrile dimer derived dyes as disclosed in EP-A-400706. The present dyes may also be used in admixture with azo dyes e.g. disperse azo dyes, anthraquinone dyes, indoaniline dyes, azomethine dyes. Examples of dyes that can be used in combination with the dyes of the present invention are disclosed in E.G. EP 92203979, EP 209,990, EP 209,991, EP 216,483, EP 218,397, EP 227,095, EP 227,090, EP 229,374, EP 235,939, EP 247,737, EP 257,577, EP 257,580, EP 258,856, EP 279,330, EP 279,467, EP 285,665, U.S. Pat. No. 4,743,582, U.S. Pat. No. 4,753,922, U.S. Pat. No. 4,753,923, U.S. Pat. No. 4,757,046, U.S. Pat. No. 4,769,360, U.S. Pat. No. 4,771,035, U.S. Pat. No. 5,026,677, JP 84/78,894, JP 84/78,895, JP 84/78,896, JP 84/227,490, JP 84/227,948, JP 85/27,594, JP 85/30,391, JP 85/229,787, JP 85/229,789, JP 85/229,790, JP 85/229,791, JP 85/229,792, JP 85/229,793, JP 85/229,795, JP 86/41,596, JP 86/268,493, JP 86/268,494, JP 86/268,495 and JP 86/284,489, U.S. Pat. No. 4,839,336, U.S. Pat. No. 5,168,094, U.S. Pat. No. 5,147,844, U.S. Pat. No. 5,177,052, U.S. Pat. No. 5,175,069, U.S. Pat. No. 5,155,088, U.S. Pat. No. 5,166,124, U.S. Pat. No. 5,166,129, U.S. Pat. No. 5,166,128, U.S. Pat. No. 5,134,115, U.S. Pat. No. 1,132,276, U.S. Pat. No. 1,132,275, U.S. Pat. No. 5,132,274, U.S. Pat. No. 5,132,273, U.S. Pat. No. 5,132,268, U.S. Pat. No. 5,132,267, U.S. Pat. No. 5,126,314, U.S. Pat. No. 5,126,313, U.S. Pat. No. 5,126,312, U.S. Pat. No. 5,126,311, U.S. Pat. No. 5,134,116, U.S. Pat. No. 4,975,410, U.S. Pat. No. 4,885,272, U.S. Pat. No. 4,886,029, etc.

The coating layer may also contain other additives, such as curing agents, preservatives, organic or inorganic fine particles, dispersing agents, antistatic agents, defoaming agents, viscosity-controlling agents, these and other ingredients have been described more fully in EP 133,011, EP 133,012, EP 111,004, and EP 279,467.

Any material can be used as the support for the dye-donor element provided it is dimensionally stable and capable of withstanding the temperatures involved, up to 400° C. over a period of up to 20 msec, and is yet thin enough to transmit heat applied on one side through to the dye on the other side to effect Transfer to the receiver sheet within such short periods, typically from 1 to 10 msec. Such materials include polyesters such as polyethylene terephthalate, polyamides, polyacrylates, polycarbonates, cellulose esters, fluorinated polymers, polyethers, polyacetals, polyolefins, polyimides, glassinc paper and condenser paper. Preference is given to a support comprising polyethylene terephthalate. In general, the support has a thickness of 2 to 30 μm. The support may also be coated with an adhesive or subbing layer, if desired.

The dye layer of the dye-donor element may be coated on the support or printed thereon by a printing technique such as a gravure process.

A dye barrier layer comprising a hydrophilic polymer may also be employed between the support and the dye layer of the dye-donor element to enhance the dye transfer densities by preventing wrong-way transfer of dye backwards to the support. The dye barrier layer may contain any hydrophilic material that is useful for the-intended purpose. In general, good results have been obtained with gelatin, polyacrylamide, polyisopropyl acrylamide, butyl methacrylate-grafted gelatin, ethyl methacrylate-grafted gelatin, ethyl acrylate-grafted gelatin, cellulose monoacetate, methylcellulose, polyvinyl alcohol, polyethyleneimine, polyacrylic acid, a mixture of polyvinyl alcohol and polyvinyl acetate, a mixture of polyvinyl alcohol and polyacrylic acid, or a mixture of cellulose monoacetate and polyacrylic acid. Suitable dye barrier layers have been described in e.g. EP 227091 and EP 228065. Certain hydrophilic polymers, e.g. those described in EP 227091. also have an adequate adhesion to the support and the dye layer, so that the need for a separate adhesive or subbing layer is avoided. These particular hydrophilic polymers used in a single layer in the dye-donor element thus perform a dual function, hence are referred to as dye-barrier/subbing layers.

Preferably the reverse side of the dye-donor element has been coated with a slipping layer to prevent the printing head from sticking to the dye-donor element. Such a slipping layer would comprise a lubricating material such as a surface active agent, a liquid lubricant, a solid lubricant or mixtures thereof, with or without a polymeric binder. The surface-active agents may be any agents known in the art such as carboxylates, sulfonates, phosphates, aliphatic amine salts, aliphatic quaternary ammonium salts, polyoxyethylene alkyl ethers, polyethylene glycol fatty acid esters, fluoroalkyl $C_2$–$C_{20}$ aliphatic acids. Examples of liquid lubricants include silicone oils, synthetic oils, saturated hydrocarbons and glycols. Examples of solid lubricants include various higher alcohols such as stearyl alcohol, fatty acids and fatty acid esters. Suitable slipping layers have been described in e.g. EP 138483, EP 227090. U.S. Pat. No. 4,567,113, U.S. Pat. No. 4,572,860, U.S. Pat. No. 4,717,711. Preferably the slipping layer comprises a styrene-acrylonitrile copolymer or a styrene-acrylonitrile-butadiene copolymer or a mixture thereof or a polycarbonate as described in EP-A-527520 as binder and a polysiloxane-polyether copolymer or polytetrafluoroethylene or a mixture thereof as lubricant in an amount of 0.1 to 10% by weight of the binder or binder mixture.

The support for the receiver sheet that is used with the dye-donor element may be a transparent film of e.g. polyethylene terephthalate, a polyether sulfone, a polyimide, a cellulose ester or a polyvinyl alcohol-co-acetal. The support may also be a reflective one such as baryta-coated paper, polyethylene-coated paper or white polyester i.e. white-pigmented polyester. Blue-coloured polyethylene terephthalate film can also be used as support.

To avoid poor adsorption of the transferred dye to the support of the receiver sheet or receiver element this support must be coated with a special surface, a aye-image-receiving layer, into which the dye can diffuse more readily. The dye-image-receiving layer may comprise, e.g. a polycarbonate, a polyurethane, a polyester, a polyamide, polyvinyl chloride. polystyrene-co-acrylonitrile, polycaprolactone or mixtures thereof. The dye-image receiving layer may also comprise a heat-cured product of poly(vinylchloride/co-vinylacetate/co-vinylalcohol) and polyisocyanate. Suitable dye-receiving layers have been described in e.g. EP 133011, EP 133012, EP 144247, EP 227094, EP 228066.

In order to improve the light-fastness and other stabilities of recorded images, UV absorbers, singlet oxygen quenchers such as HALS-compounds (Hindered Amine Light Stabilizers) and/or antioxidants can be incorporated into the receiving layer.

The dye layer of the dye-donor element or the dye-image-receiving layer of the receiver sheet may also contain a releasing agent that aids in separating the dye-donor element from the receiving sheet after transfer. The releasing agents can also be incorporated in a separate layer on at least part of the dye layer and/or of the dye-image-receiving layer. Suitable releasing agents are solid waxes, fluorine- or phosphate-containing surface-active agents and silicone oils. Suitable releasing agents have been described in e.g. EP 133012, JP 85/19138 and EP 227092.

The dye-donor elements according to the invention can be used to form a dye transfer image, which process comprises placing the dye layer of the dye-donor element in face-to-face relation with the dye-image-receiving layer of the receiver sheet or receiver element and image-wise heating preferably from the back of the dye-donor element. The transfer of the dye is preferably accomplished by hearing for about several milliseconds at a temperature of 400° C.

When the process is performed for but one single color, a monochrome dye transfer image is obtained. A multicolor image can be obtained by using a dye-donor element containing three or more primary colour dyes and sequentially performing the process steps described above for each colour. After the first dye has been transferred, The elements are peeled apart. The above sandwich of dye-donor element and receiver sheet is formed on three occasions during The time when heat is applied by the thermal printing head. After the first dye has been transferred, the elements are peeled apart. A second dye-donor element (or another area of the dye-donor element with a different dye area) is then brought in register with the dye-receiving element and the process is repeated. The third colour and optionally further colours are obtained in the same manner.

In addition to thermal heads, laser light, infrared flash or heated pens can be used as the heat source for supplying heat energy. Thermal printing heads that can be used to transfer dye from the dye-donor elements of the present invention to a receiver sheet are commercially available. In case laser light is used, the dye layer or another layer of the dye element has to contain a compound that absorbs the light emitted by the laser and converts it into heat e.g. carbon black.

Alternatively, the support of the dye-donor element may be an electrically resistive ribbon consisting of e.g. a multilayer structure of a carbon loaded polycarbonate coated with a thin aluminum film. Current is injected into the resistive ribbon by electrically adressing a printing head electrode resulting in highly localized heating of the ribbon beneath the relevant electrode. The fact that in this case the heat is generated directly in the resistive ribbon and that it is thus the ribbon that gets hot leads to an inherent advantage in printing speed using the resistive ribbon/electrode head technology compared to the thermal head technology, according to which the various elements of the thermal head get hot and must cool down before the head can move to the next printing position.

The following examples illustrate the invention in more detail without limiting, however, the scope thereof.

EXAMPLE 1—Synthesis of III.21

By way of example the preparation of dyes III.21, III.24, IV.1, VI.3 are described. All other compounds mentioned in tables 1 to 6 and the preparation of compound 11.6 are prepared in the same way and the starting materials can be prepared according to literature procedures known to those who are skilled in the art of organic synthesis.

Dye III.21 is prepared according to scheme 1.

Scheme 1

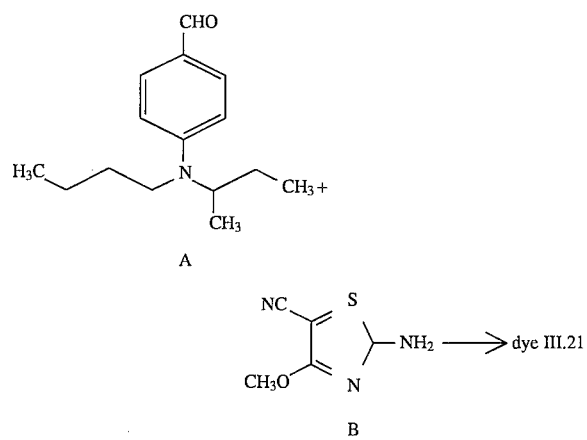

15.8 g of compound A and 10.0 g of compound B (prepared according to EP94201737) are dissolved in 120 ml of toluene, A catalytic amount of methanesulfonic acid is added and the solution is refluxed for 4 hours while removing water azeotropically. The solvent is removed under reduced pressure and the residual oil is purified by column chromatography. 15.4 g of dye III.21 are obtained as an oil.

EXAMPLE 2—Synthesis of dye III.24

2.0 g of dye 111.21 and 0.4 g of potassium cyanide are dissolved in 20 ml of dimethylsulfoxide. The solution is stirred for one hour at room temperature followed by the addition of a solution of 0.8 g 1.3-dibromo-5.5-dimethyl-hydantoin in 1 ml of dimethylacetamid. Stirring is continued for 10 minutes. Dichloromethane is added and the solution is washed with water, dried and concentrated. The residue is crystallized from methanol to obtain 0.9 g of pure dye 111.24 (mp. 122° C.).

EXAMPLE 3—Synthesis of dye IV.1

Dye IV.1 is prepared according to scheme 2.

Scheme 2

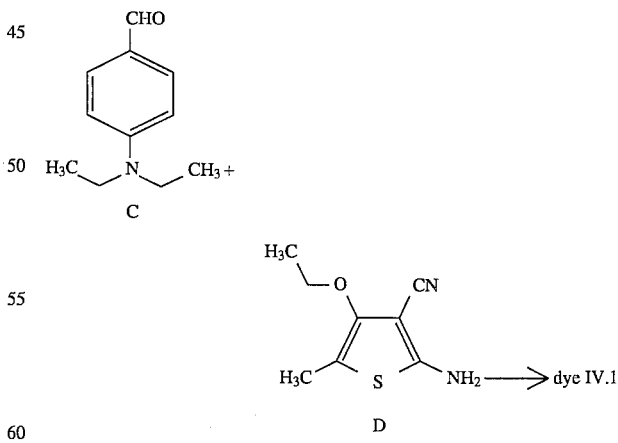

9.7 g of compound C and 10 g of compound Dane dissolved in 100 ml of ethanol. A catalytic amount of methanesulfonic acid is added and the solution is refluxed for two hours. After cooling the crystals are filtered, washed with methanol and dried. 10 g of dye IV.1 are obtained (mp. 113° C.).

EXAMPLE 4—Synthesis of dye VI.3

Dye VI.3 is prepared according to scheme 4.

Scheme 4

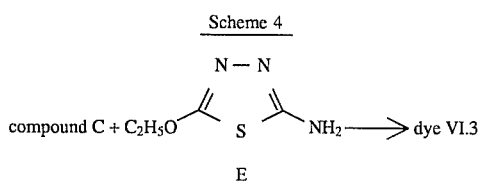

9.7 g of compound C and 8 g of compound E are dissolved in 100 ml of toluene. A catalytic amount of methanesulfonic acid is added and water is removed azeotropically. The solution is concentrated under reduced pressure and the residue is solidified with methanol to obtain 12.6 g of dye VI.3. Pure dye VI.3 is obtained by crystallization from ethanol (9.1 g: mp. 138° C.).

EXAMPLE 5—Synthesis of a thermochromic comopund; compound II.6

Compound II.6 is prepared according to scheme 5.

Scheme 5

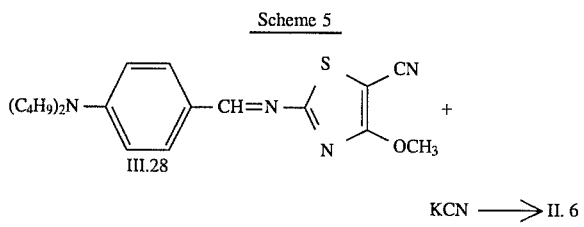

A solution of 2.0 g of dye III.28 and 0.8 g of potassium cyanide in 20 ml of dimethylsulfoxide is stirred for one hour at room temperature. The solution is poured into a mixture of dichloromethane/methanol/water. The organic layer is dried and concentrated under reduced pressure. The residue is purified by column chromatography to obtain 1.6 g of pure compound II.6. When heated compound II.6 is transformed in dye III.28 at 103° C.

EXAMPLE 6

The absorption maxima ($\lambda_{max}$) and molar extinction coefficients ($\epsilon$) of some dyes and leuco dyes (thermochromic compounds) identified below were determined in methanol unless otherwise stated. The results are listed in table 7.

TABLE 7

| Dye | $\lambda_{max}$ (nm) | $\epsilon$ (mol$^{-1}$ cm$^{-1}$ 1) |
|---|---|---|
| III.5 | 454 | 33201 |
| III.8 | 534 | 45133 |
| III.9 | 530 | 46868 |
| III.14 | 450 | 38301 |
| III.1 | 456 | 42840 |
| III.2 | 456 | 49446 |
| III.34 | 466 | 47583 |
| III.21 | 460 | 52265 |
| III.24 | 534 | 47852 |
| III.35 | 518 | 36686 |
| III.28 | 460 | 50514 |
| III.29 | 458 | 49507 |
| III.3 | 456 | 46649 |
| III.30 | 458 | 49247 |
| III.31 | 534 | 43520 |
| III.32 | 534 | 46558 |
| III.7 | 534 | 45056 |

TABLE 7-continued

| Dye | $\lambda_{max}$ (nm) | $\epsilon$ (mol$^{-1}$ cm$^{-1}$ 1) |
|---|---|---|
| III.33 | 534 | 47427 |
| III.50 | 466 | 48572 |
| III.22 | 458 | 51595 |
| III.25 | 534 | 44824 |
| III.51 | 454 | 44844 |
| III.52 | 460 | 44596 |
| III.53 | 454 | 48223 |
| III.54 | 510 | 42365 |
| III.23 | 458 | 33233 |
| IV.1 | 438 | 43022 |
| IV.14 | 442 | 46350 |
| IV.15 | 446 | 44277 |
| IV.27 | 442 | 42280 |
| IV.37 | 466 (CH$_2$Cl$_2$) | 65879 |
| IV.19 | 472 | 43865 |
| IV.3 | 486 | 31576 |
| IV.4 | 570 (CH$_2$Cl$_2$) | 57083 |
| IV.39 | 476 (+N(C$_2$H$_5$)$_3$) | 67451 |
| IV.38 | 472 (+N(C$_2$H$_5$)$_3$) | 66119 |
| V.18 | 474 (CH$_2$Cl$_2$) | 74078 |
| VI.1 | 436 | 53580 |
| VI.6 | 422 | 48544 |
| VI.3 | 414 | 49375 |
| VI.7 | 418 | 45851 |
| VI.8 | 424 (+N(C$_2$H$_5$)$_3$) | 43606 |
| VI.9 | 418 | 46309 |
| VI.10 | 416 | 49474 |
| II.1 | 276 (300) | 25734 |
|  | 208 | 25747 |
| II.7 | 276 (300) | 26765 |
|  | 210 | 26813 |
| V.1 | 426 | 55642 |
| D.1 | 428 | 50368 |
| D.2 | 460 | 41827 |
| D.3 | 480 | 37498 |
| D.10 | 428 | 50738 |
| D.11 | 430 | 53015 |
| D.15 | 514 (CH$_2$Cl$_2$) | 46827 |
| D.9 | 486 | 41143 |
| D.14 | 486 | 28987 |

EXAMPLE 7

Receiver sheets were prepared by coating a subbed polyethylene terephthalate film having a thickness of 175 μm with a dye-image-receiving layer from a solution in ethyl methyl ketone of 3.6 g/m$^2$ of poly(vinyl chloride/co-vinyl acetate/co-vinyl alcohol). (Vinylite VAGD supplied by Union Carbide), 0.336 g/m$^2$ of polyisocyanate (Desmodur N75 supplied by Bayer AG), and 0.2 g/m$^2$ of hydroxymodified polydimethylsiloxane (Tegomer H SI 2111 supplied by Goldschmidt).

Dye-donor elements for use according To thermal dye sublimation transfer were prepared as follows.

A solution in methyl ethyl ketone of 0.5% by weight of dye and 0.5% by weight of poly(styrene-co-acrylonitrile) (PSA) (Luran 388s, supplied by BASF Germany) as a binder was prepared.

A dye layer having a wet thickness of 100 μm was coated from this solution on a polyethylene terephthalate film support having a thickness of 6 μm and carrying a conventional subbing layer. The resulting dye layer was dried by evaporation of the solvent.

The opposite side of the film support was coated with a subbing layer of a copolyester comprising ethylene glycol, adipic acid, neopentyl glycol, terephthalic acid, isophthalic acid, and glycerol.

The resulting subbing layer was covered with a solution in methyl ethyl ketone of 0.5 g/m$^2$ of a polycarbonate having the following structural formula go form a heat resistant layer:

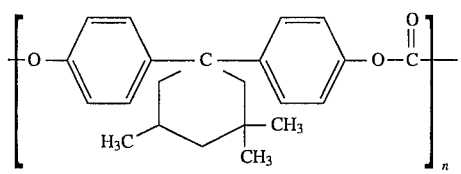

wherein n has a value giving a polycarbonate with a relative viscosity of 1.295 (measured in a 0.5% by weight solution in dichloromethane).

Finally, a top layer of polyether-modified polydimethylsiloxane (Tegoglide 410, Goldschmidt) was coated from a solution in isopropanol on the resulting heat-resistant polycarbonated layer.

The dye-donor element was printed in combination with a receiver sheet in a Mitsubishi colour video printer CP100E.

The receiver sheet was separated from the dye-donor element and the colour density value of the recorded image was measured by means of a Macbeth TR 924 densitometer in the red, green, and blue regions in status A mode.

The above described experiment was repeated for each of the dyes identified in table 8 hereinafter. The results are also given in table 8.

TABLE 8

| Dye | $D_{max}$ in transmission | Spectral absorption in Status A behind filter in reflex | | |
|---|---|---|---|---|
| | | Red | Green | Blue |
| III.5 | 174 | 15 | 54 | 150 |
| III.23 | 130 | 14 | 58 | 150 |
| III.14 | 188 | 15 | 31 | 150 |
| III.2 | 247 | 14 | 39 | 150 |
| III.1 | 284 | 14 | 40 | 150 |
| III.9 | 302 | 48 | 150 | 57 |
| III.8 | 263 | 45 | 150 | 50 |
| III.21 | 220 | 10 | 47 | 150 |
| III.34 | 214 | 14 | 69 | 150 |
| III.24 | 275 | 41 | 150 | 34 |
| III.35 | 248 | 29 | 150 | 61 |
| III.28 | 229 | 14 | 45 | 150 |
| III.29 | 238 | 14 | 43 | 150 |
| III.3 | 246 | 13 | 78 | 150 |
| III.30 | 232 | 14 | 43 | 150 |
| III.31 | 244 | 39 | 150 | 36 |
| III.32 | 289 | 37 | 150 | 37 |
| III.7 | 260 | 32 | 150 | 38 |
| III.33 | 271 | 37 | 150 | 36 |
| III.50 | 203 | 10 | 64 | 150 |
| III.22 | 192 | 10 | 45 | 150 |
| IV.1 | 270 | 10 | 17 | 150 |
| IV.14 | 212 | 10 | 18 | 150 |
| IV.15 | 197 | 10 | 25 | 150 |
| IV.19 | 133 | 10 | 119 | 150 |
| IV.37 | 41 | | | |
| IV.38 | 85 | 10 | 97 | 150 |
| IV.39 | 89 | 10 | 120 | 150 |
| VI.1 | 235 | 10 | 14 | 150 |
| VI.6 | 213 | 10 | 14 | 150 |
| VI.3 | 165 | 10 | 13 | 150 |
| VI.7 | 198 | 11 | 15 | 150 |
| VI.8 | 241 | 10 | 14 | 150 |
| VI.9 | 197 | 11 | 14 | 150 |

EXAMPLE 8

Receiver sheets were prepared as described in example 7. Black dye donor elements were prepared as follows : The amounts of dyes as indicated in the following table 9 were added each time to 10 ml of a solution of 0.5% by weight of poly(styrene-co-acrylonitrile) (Luran 388s. supplied by BASF Germany) in ethyl methyl ketone. The resulting black coloured dye mixtures were coated, printed, and evaluated as described in the above Example 7, the maximum densities being measured in transmission.

The results of the tests are listed in the following table 9. The prior art dyes C-magenta 1, C-magenta 2. C-cyan, C-yellow 1 and C-yellow 2 having the following structural formulae were used for comparison in the tests.

C-magenta 1

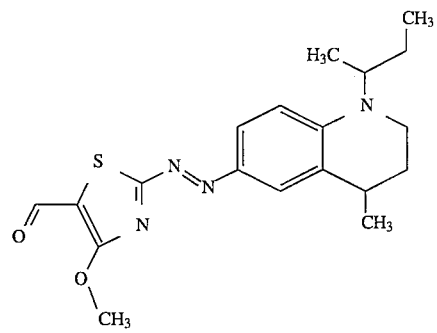

C-magenta 2

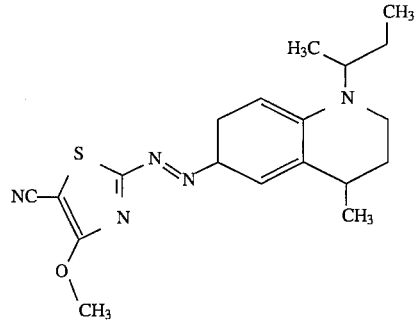

C-cyan

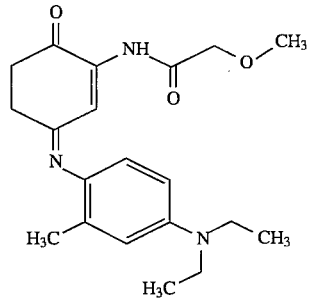

C-yellow 1

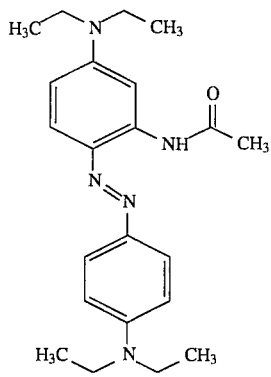

C-yellow 2

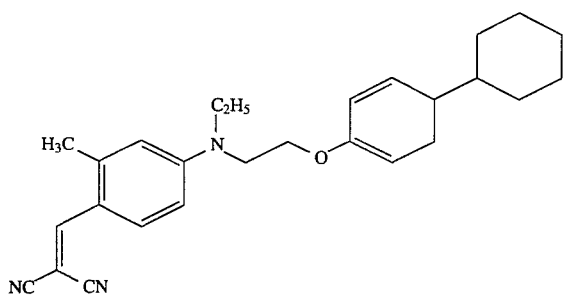

The above dyes can be prepared as described or indicated in U.S. Pat. No. 5,169,828 and the corresponding EP 453,020.

TABLE 9

| Test No. | Amount of dye Dye | Status A in mg | Spectral absorption behind filter |  |  |  |
|---|---|---|---|---|---|---|
|  |  |  | Red | Green | Blue | Visual |
| 1 | C-cyan | 23 | 170 | 208 | 206 | 198 |
|  | C-magenta 1 | 7 |  |  |  |  |
|  | C-magenta 2 | 31 |  |  |  |  |
|  | C-yellow 1 | 18 |  |  |  |  |
|  | C-yellow 2 | 31 |  |  |  |  |
| 2* | Yellow III.23 | 31 | 166 | 225 | 175 | 203 |
| 3* | Yellow III.28 | 31 | 174 | 232 | 221 | 210 |
| 4* | Yellow III.29 | 31 | 183 | 242 | 232 | 218 |
| 5* | Yellow III.3 | 31 | 184 | 238 | 217 | 218 |
| 6* | Yellow III.30 | 31 | 183 | 240 | 209 | 218 |
| 7* | Yellow III.34 | 31 | 181 | 254 | 205 | 219 |

*In the tests No. 2, 3, 4, 5, 6, 7 C-yellow 2 was changed for a color dye according to the invention. The quantities of the other colour dyes for compounding the black mixture are the same as in comparison Test No. 1.

The results listed in Table 9 show that by means of dye-donor elements incorporating a dye mixture comprising a dye according to the invention, transferred dye images with high density black values can be obtained.

I claim:

1. Dye donor element comprising on a support a dye layer, said dye layer comprising a binder and a dye according to formula (I):

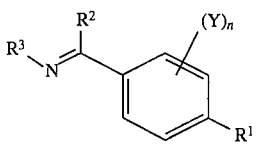

wherein:

$R^1$ represents $NR^4R^5$, $OR^6$ or $SR^6$, $R^2$ represents hydrogen cyano $COR^7$, $CO_2R^7$, $CONR^8R^9$, $SO_2R^{10}$, Y represents any substituent, n represents 0, 1, 2, 3 or 4, said Y substituents being the same or different when n is greater than 1 or said Y substituents can form an annelated ring system;

$R^3$ is The residue of a heterocyclic amine $R^3$—$NH_2$, $R^4$, $R^5$, $R^6$, $R^7$, $R^8$ and $R^9$ each independently represent hydrogen, an alkyl, an alkenyl, an alkynyl, an aryl, a heterocyclic ring or $R^4$ and $R^5$ together represent the necessary atoms to form a 5- or 6-membered ring or $R^4$ and/or $R^5$ together with one of the Y-substituents represent the necessary atoms to form a 5- or 6-membered, fused-on heterocyclic ring system or $R^8$ and $R^9$ together represent the necessary atoms to form a 5- or 6-membered ring or $R^7$ or $R^8$ or $R^9$ or $R^8$ and $R^9$ together with one of the Y-substituents represent the necessary atoms to form a 5- or 6-membered, fused-on heterocyclic ring system, $R^{10}$ represents hydroxy, alkoxy, aryloxy, $NR^{11}R^{12}$, aryl or alkyl or $R^{10}$ together with one of the Y-substituents represent the necessary atoms to form a 5- or 6-membered, fused-on heterocyclic ring system, $R^{11}$ and $R^{12}$ each independently represent hydrogen, an alkyl, an alkenyl, an alkynyl, an aryl, a heterocyclic ring or $R^{11}$ and $R^{12}$ together represent the necessary atoms to form a 5- or 6-membered ring.

2. A dye donor element according to claim 1 wherein said dye corresponds to the following formula (III):

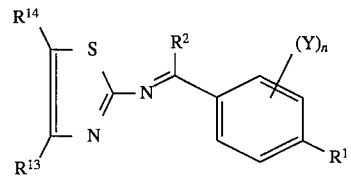

wherein $R^1$, $R^2$, Y and n have the same meaning as defined in general formula (I) of claim 1, $R^{13}$ and $R^{14}$ each independently represent hydrogen, alkyl, aryl, alkenyl, alkynyl, alkoxy, aryloxy, thioalkyl, thioaryl, halogen, amino, $NO_2$, CN, acyloxy, acylamino, sulfonamido, sulfonylamino, a heterocyclic group, $POR^{15}R^{16}$, a sulfonyl group or $R^{17}$—C=A;

$R^{15}$ and $R^{16}$ each independently represent alkyl, alkenyl, aryl, alkyloxy, aryloxy, alkylthio, arylthio, amine or a heterocyclic group or $R^{15}$ and $R^{16}$ together represent the necessary atoms to form a 5- or 6-membered ring;

$R^{17}$ represents hydrogen, an alkyl, an aryl, an aryloxy group, an alkoxy group, an alkylthio group, an amine group, an electron withdrawing group or $R^{17}$ together with $R^{19}$, $R^{20}$ or $R^{18}$ represent the necessary atoms for completing a ring system:

A represents O, N—$R^{18}$, $CR^{19}R^{20}$;

$R^{18}$ represents H, CN, $NR^{21}R^{22}$, $OR^{21}$, $OCOR^{21}$, $OCO_2R^{21}$, $OCONR^{21}R^{22}$, $OSO_2R^{21}$, $OP(O)(OR^{21})(OR^{22})$, alkyl, aryl, a heterocyclic ring;

$R^{19}$ and $R^{20}$ independently represent a heterocyclic ring of an electron withdrawing group or $R^{19}$ and $R^{20}$ together represent the necessary atoms for completing a ring system;

$R^{21}$ and $R^{22}$ independently represent hydrogen, alkyl, aryl, a heterocyclic ring or $R^{21}$ and $R^{22}$ together represent the atoms necessary for completing a heterocyclic ring.

3. A dye donor element according to claim 1 wherein said dye corresponds to the following formula (IV):

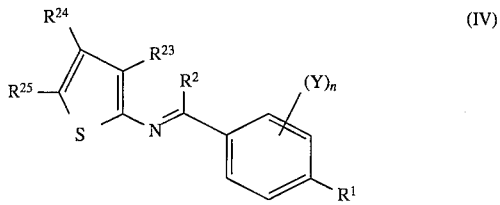

wherein $R^1$, $R^2$, Y and n have the same meaning as defined in formula (I) of claim 1:

$R^{23}$ represents hydrogen, cyan or an electron withdrawing group;

$R^{24}$ represents hydrogen, halogen, alkoxy, alkyl, aryl, amino, acylamido, CN, alkylthio, a carbocylic ester, a carboxylic amide, a sulfonate, a sulfonamide, a heterocyclic group, an aryloxy, acyloxy, arylthio, an imino group;

$R^{25}$ represents hydrogen, CN, alkyl, aryl, halogen, $NO_2$, a sulfonyl group, a sulfonate group, a sulfonamido group or $R^{17}$—C=A wherein $R^{17}$ and A have the same meaning as defined in formula (III) of claim 2, or $R^{24}$ and $R^{25}$ or $R^{24}$ and $R^{23}$ together represent the necessary atoms for completing a ring system.

4. A dye donor element according to claim 1 wherein said dye corresponds to the following general formula (V):

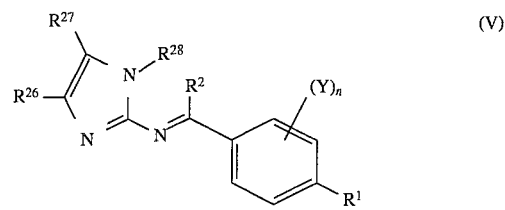

wherein $R^1$, $R^2$, Y and n have the same meaning as defined in formula (I) of claim 1;

$R^{26}$ and $R^{27}$ each independently represent hydrogen, alkyl, aryl, alkenyl, alkynyl, alkoxy, aryloxy, thioalkyl, thioaryl, halogen, amino, $NO_2$, CN, acyloxy, acylamino, sulfonamido, sulfonylamino, a heterocyclic group, $POR^{15}R^{16}$, a sulfonyl group or $R^{17}$—C=A, $R^{15}$, $R^{16}$, $R^{17}$ and A have the same meaning as defined in formula (III) of claim 2;

$R^{28}$ represents hydrogen, alkyl, aryl, acyl or sulfonyl;

$R^{27}$ and $R^{28}$, or $R^{26}$ and $R^{27}$ together represent the necessary atoms for completing a ring system.

5. A dye donor element according to claim 1 wherein said dye corresponds to the following general formula (VI):

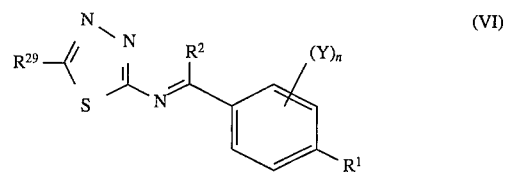

wherein $R^1$, $R^2$, Y and n have the same meaning as defined in formula (I) of claim 1:

$R^{29}$ represents any substituent.

* * * * *

UNITED STATES PATENT AND TRADEMARK OFFICE
CERTIFICATE OF CORRECTION

PATENT NO. : 5,547,815
DATED : August 20, 1996
INVENTOR(S) : Luc Vanmaele

It is certified that error appears in the above-identified patent and that said Letters Patent is hereby corrected as shown below:

Column 2, line 19, "Thereon" should read --thereon--;

Column 2, line 30, "cyanoCOR$^7$" should read --cyano, COR$^7$--;

Column 2, line 36, "Than" should read --than--;

Column 2, line 58, "The" should read --the--;

Column 3, line 17, "thiazoiyl" should read --thiazolyl--;

Column 4, line 23, "R$^{19}$..." should follow after "with" on the preceding line;

Column 4, line 30, "alkyl aryl" should read --alkyl, aryl,--;

Column 4, line 43, "R$^{22}$..." should follow after "and" on the preceding line;

UNITED STATES PATENT AND TRADEMARK OFFICE
CERTIFICATE OF CORRECTION

PATENT NO. : 5,547,815
DATED : August 20, 1996
INVENTOR(S) : Luc Vanmaele

It is certified that error appears in the above-identified patent and that said Letters Patent is hereby corrected as shown below:

Col. 9, last line,

"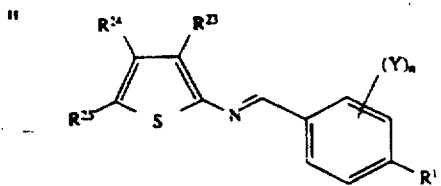"

should read

--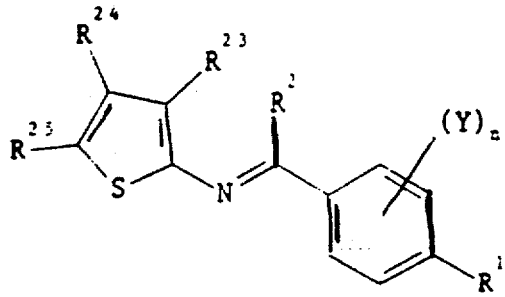--

UNITED STATES PATENT AND TRADEMARK OFFICE
CERTIFICATE OF CORRECTION

PATENT NO. : 5,547,815
DATED : August 20, 1996
INVENTOR(S) : Luc Vanmaele

It is certified that error appears in the above-identified patent and that said Letters Patent is hereby corrected as shown below:

Column 23, line 57 (Compound II.10), "$N(C_4H_9)_2$" should read --$N(C_2H_5)_2$--;

Column 24, line 32, "inkier" should read --inkjet--;

Column 24, line 50, "To" should read --to--;

Column 24, line 55, "cellulese" should read --cellulose--;

Column 24, line 61, "burytel-vinyl" should read --butyral-vinyl--;

Column 25, line 16, "EP 227,090" should read --EP 227,096--;

Column 25, line 48, "Transfer" should read --transfer--;

Column 25, line 53, "glassinc" should read --glassine--;

Column 27, line 21, "The" should read --the--;

Column 27, line 23, "The" should read --the--;

Column 28, line 22, "toluene," should read --toluene.--;

Column 28, line 30, "111.21" should read --III.21--;

Column 28, line 38, "111.24" should read --III.24--;

Column 28, line 62, "Dane" should read --D are--;

UNITED STATES PATENT AND TRADEMARK OFFICE
CERTIFICATE OF CORRECTION

PATENT NO. : 5,547,815

DATED : August 20, 1996

INVENTOR(S) : Luc Vanmaele

It is certified that error appears in the above-identified patent and that said Letters Patent is hereby corrected as shown below:

Column 29, line 13, "100 mi" should read --100 ml--;

Column 30, line 50, "To" should read --to--;

Column 31, line 1, "go" should read --to--;

Col. 33, line 40,

"
| Test No. | Dye | Amount of dye in mg | Spectral absorption in Status A behind filter | | | |
|---|---|---|---|---|---|---|
| | | | Red | Green | Blue | Visual |

"

should read

--
| Test No. | Dye | Amount of dye in mg | Spectral absorption in Status A behind filter | | | |
|---|---|---|---|---|---|---|
| | | | Red | Green | Blue | Visual |

UNITED STATES PATENT AND TRADEMARK OFFICE
CERTIFICATE OF CORRECTION

PATENT NO. : 5,547,815
DATED : August 20, 1996
INVENTOR(S) : Luc Vanmaele

It is certified that error appears in the above-identified patent and that said Letters Patent is hereby corrected as shown below:

<u>Column 34, line 9</u>, "hydrogen cyano $COR^7$" should read --hydrogen, cyano, $COR^7$--;

<u>Column 34, line 16</u>, "The" should read --the--;

<u>Column 34, line 54</u>, "amine" should read --amino--;

<u>Column 35, line 2</u>, "of an" should read --or an--.

Signed and Sealed this

Fifth Day of August, 1997

Attest:

Attesting Officer

BRUCE LEHMAN
Commissioner of Patents and Trademarks